US 6,749,838 B1

(12) United States Patent
Joichi et al.

(10) Patent No.: US 6,749,838 B1
(45) Date of Patent: Jun. 15, 2004

(54) COSMETIC SUNSCREEN PREPARATION (75) Inventors: Kyoko Joichi, Kanagawa (JP); Katsuki Ogawa, Kanagawa (JP); Kazuhisa Ohno, Kanagawa (JP); Akio Nasu, Kanagawa (JP)

(73) Assignee: Shiseido Company, Ltd, Tokyo (JP)

( * ) Notice: Subject to any disclaimer, the term of this patent is extended or adjusted under 35 U.S.C. 154(b) by 0 days.

(21) Appl. No.: 09/807,750

(22) PCT Filed: Aug. 18, 2000

(86) PCT No.: PCT/JP00/05547

§ 371 (c)(1),
(2), (4) Date: Apr. 18, 2001

(87) PCT Pub. No.: WO01/13874

PCT Pub. Date: Mar. 1, 2001

(30) Foreign Application Priority Data

Aug. 19, 1999 (JP) .............................. 11-232832
Aug. 16, 2000 (JP) ......................... 2000-246895

(51) Int. Cl.[7] ............................ A61K 7/42; A61K 7/44; A61K 7/035
(52) U.S. Cl. .......................... 424/59; 424/401; 424/47; 424/60; 424/69; 424/64; 424/67
(58) Field of Search ............... 424/59, 69, 60, 424/64, 67

(56) References Cited

U.S. PATENT DOCUMENTS 5,914,101 A * 6/1999 Tapley et al. .................. 424/59
6,428,795 B2 * 8/2002 Miura et al. ................. 424/401
6,482,441 B1 * 11/2002 Hasegawa et al. ........... 424/490

FOREIGN PATENT DOCUMENTS

WO          9630449     * 10/1996

OTHER PUBLICATIONS

Translated Abstract of Japanese Patent Application No. 2000–246895, Date of Filing Aug. 16, 2000, with Figure 1A and 1B. Neither the Application nor the Abstract have been published.

Japanese Patent Office, "Patent Abstracts of Japan", Publication No.: 2001–058934, Date of Publication: Mar. 06, 2001, Application No. 11–232832, Date of Filing Aug. 19, 1999. Published in Japanese language only.

Japanese Patent Office, "Patent Abstracts of Japan", Publication No.: 11–302015, Date of Publication: Nov. 02, 1999, Application No.: 10–336316, Date of Filing: Nov. 26, 1998.

Japanese Patent Office, "Patent Abstracts of Japan", Publication No.: 11–193354, Date of Publication: Jul. 21, 1999, Application No.: 09–370480, Date of Filing: Dec. 26, 1997.

(List continued on next page.)

Primary Examiner—Sabiha Qazi
(74) Attorney, Agent, or Firm—Snider & Associates; Ronald R. Snider (57) ABSTRACT An object of the present invention is to provide a sunscreen cosmetic in which a micro particle zinc oxide is dispersed satisfactorily and which is excellent in the ultraviolet rays protection effect as indicated by SPF and PFA, and also in the finish transparency and the system stability.

A sunscreen cosmetic obtained by means of an incorporation of a composite powder of a micro particle zinc oxide having a particle size of 0.1 μm or less which is coated with a silicic anhydride at a coating rate of 5 to 30 wt % and whose surface is treated with a silicone of 3 to 12 wt %, a dispersing treatment of said composite powder in an oil or water using a media-agitating mill or a high pressure dispersing machine and/or an incorporation of a polyoxyalkylene-modified polysiloxane.

19 Claims, 1 Drawing Sheet

OTHER PUBLICATIONS

Japanese Patent Office, "Patent Abstracts of Japan", Publication No.: 10–130130, Date of Publication: May 19, 1998, Application No.: 08–300916, Date of Filing: Oct. 24, 1996.
Japanese Patent Office, "Patent Abstracts of Japan", Publication No.: 07–167781, Date of Publication: Jul. 04, 1995, Application No.: 06–229930, Date of Filing: Sep. 26, 1994.
Japanese Patent Office, "Patent Abstracts of Japan", Publication No.: 03–072932, Date of Publication: Mar. 28, 1991, Application No.: 01–192554, Date of Filing: Jul. 27, 1989.
Japanese Patent Office, "Patent Abstracts of Japan", Publication No.: 61–037711, Date of Publication: Feb. 22, 1986, Application No.: 59–161134, Date of Filing: Jul. 31, 1984.

* cited by examiner

COSMETIC SUNSCREEN PREPARATION

This application claims the priority of Japanese Patent Application No. 11-232832 filed on Aug. 19, 1999 and Japanese Patent Application No. 2000-246895 file on Aug. 16, 2000 which are incorporated herein by reference.

TECHNICAL FIELD

The present invention relates to a sunscreen cosmetic containing a micro particle zinc oxide, especially to the improvement thereof in the stability and the ultraviolet rays protection effect.

BACKGROUND ART

Conventionally, a sunscreen cosmetic contains a large amount of a micro particle zinc oxide for the purpose of protecting skin from a long-waved ultraviolet light. In a case where a micro particle zinc oxide is added mainly to a sunscreen cosmetic of a W/O emulsion type, a micro particle zinc oxide whose particulate surface is imparted with a hydrophobicity has generally been employed. Such hydrophobicity-imparting treatment is effected for example with a silicone, a metallic soap, a fatty acid, a fluoride and the like.

However, a highly dispersed state of such surface-treated micro particle zinc oxide is achieved only with an extreme difficulty, due to which a satisfactory ultraviolet rays protection effect can not actually be obtained. Such highly dispersed state, when accomplished using a media-agitating mill or a high pressure dispersing machine, results in an improvement in the ultraviolet rays protection effect. Nevertheless, a surface treatment coating may be peeled off to expose a non-treated hydrophilic surface which leads to an aggregation of a particle in an aqueous phase as well as a susceptibility to a reaction with a free fatty acid present in the system to form a gel, resulting in an extremely poor stability during a prolonged storage period.

DISCLOSURE OF INVENTION

The present invention is established in view of the problems discussed above, and thus its objective is to provide a sunscreen cosmetic in which a micro particle zinc oxide is dispersed satisfactorily and which is excellent in the ultraviolet rays protection effect as indicated by SPF (sun protection factor) and PFA (protection factor of UVA), and also in the finish transparency and the system stability.

The inventors discovered that a composite powder obtained by treating the surface of a micro particle zinc oxide in a form close to a primary particle with a silicic anhydride followed by performing a silicone treatment can readily and highly be dispersed by a polyoxyalkylene-modified polysiloxane. Also, the inventors discovered that this is associated also with an efficient improvement in SPF and PFA of a sunscreen cosmetic. Furthermore, this composite powder undergoes no reaction with a free fatty acid in the system (a gelation reaction due to the formation of a metallic soap) resulted from the presence of a fatty acid or a fatty acid soap employed as a particle dispersing agent or a surface treating agent. Accordingly, it was discovered that the viscosity of the system was kept stably to give a use feeling which was maintained in a favorable condition.

A silicone-treated composite powder described above undergoes no reaction with water due to the exposure of a non-treated surface even when subjected to a strong mechanical force such as those exerted by a media-agitating mill or a high pressure dispersing machine. In addition, this composite powder undergoes no reaction with a free fatty acid in the system due to a fatty acid or a fatty acid soap which is employed as a dispersing agent or a surface treating agent for other powders. Accordingly, it was discovered that a favorable use feeling was maintained. Furthermore, it discovered that a highly dispersed powder served to improve SPF and PFA of a sunscreen cosmetic efficiently.

Namely, in the first aspect of the present invention, a sunscreen cosmetic is obtained by means of an incorporation of a composite powder of a micro particle zinc oxide which is coated with a silicic anhydride and whose surface is treated with a silicone, a dispersing treatment of said composite powder in an oil or water using a media-agitating mill or a high pressure dispersing machine and/or an incorporation of a polyoxyalkylene-modified polysiloxane.

In a sunscreen cosmetic of the present invention, it is preferable that said polyoxyalkylene-modified polysiloxane is one or more selected from those represented by general formulae [1], [2] and [3]:

(in general formulae [1], [2] and [3], R denotes a methyl group or partly a phenyl group, R denotes hydrogen or an alkyl group having 1 to 12 carbon atoms, p denotes an integer of 1 to 5, q denotes an integer of 2 to 3, and x, m and n denote mean numbers giving a polyoxyalkylene-modified organopolysiloxane which contains in its molecule 5 to 40 wt % of the polyoxyalkylene group and whose molecular weight is 2000 or more.)

Also in a sunscreen cosmetic of the present invention, it is preferable that said composite powder is a composite powder obtained by coating a microparticulate zinc oxide having a particle size of 0.1 μm or less with a silicic anhydride at a coating rate of 5 to 30 wt % followed by a surface treatment with 3 to 12 wt % of a silicone.

Also in a sunscreen cosmetic of the present invention, it is preferable that said composite powder of a micro particle zinc oxide treated with a silicic anhydride and a silicone is incorporated in an amount of 3 to 30 wt % and said polyoxyalkylene-modified polysiloxane is incorporated in an amount of 0.5 to 7 wt %.

In the second aspect of a sunscreen cosmetic of the present invention, 1 wt % or more of a powder whose surface is treated with one or more substances selected from fatty acids, fatty acid soaps and fatty acid esters is further contained.

In the third aspect of a sunscreen cosmetic of the present invention, 0.1 wt % or more of one or more substances selected from fatty acids, fatty acid soaps and fatty acid esters are further incorporated as a surface treating agent for a powder.

BEST MODE FOR CARRYING OUT THE INVENTION

The present invention relates to a sunscreen cosmetic exhibiting a satisfactory dispersion of a micro particle zinc oxide as well as excellent stability and ultraviolet rays protection effect. Namely, a micro particle zinc oxide is readily and highly dispersed by means of a surface treatment with a silicic anhydride and a silicone and by an incorporation of a polyoxyalkylene-modified polysiloxane. The present invention is relates to a sunscreen cosmetic obtained by the technical approach described above, which has an excellent ultraviolet rays protection effect and a satisfactory stability with no reaction with a free fatty acid being allowed to occur.

Also, a micro particle zinc oxide treated with a silicic anhydride and a silicone is highly dispersed using a media-agitating mill or a high pressure dispersing machine. The present invention relates to a sunscreen cosmetic obtained by the technical approach described above, which has an excellent ultraviolet rays protection effect and a satisfactory stability with no reaction with a free fatty acid being allowed to occur.

Especially by combining a composite powder obtained by coating a micro particle zinc oxide whose particle size is 0.1 μm or less with a silicic anhydride at a coating rate of 5 to 30 wt % followed by a further surface treatment with a silicone with a polyoxyalkylene-modified polysiloxane, the micro particle zinc oxide can be brought into a highly dispersed condition which can not be achieved so far. Accordingly, the ultraviolet rays protection effect of a sunscreen cosmetic can be improved. Also in the present invention, by dispersing a silicone-treated composite powder by a strong mechanical force using a media-agitating mill or a high pressure dispersing machine, a micro particle zinc oxide can be brought into a finely dispersed condition which can not be achieved so far, and the ultraviolet rays protection effect of a sunscreen cosmetic can be improved.

In a silicone-treated composite powder described above, a micro particle zinc oxide is coated uniformly with a silicic anhydride. Accordingly, the elution of a zinc ion into the system is suppressed to prevent the formation of a metallic soap as a result of the reaction with a free fatty acid. Moreover, even when a strong mechanical force is exerted by a media-agitating mill or a high pressure dispersing machine, there is no inconvenience that a surface treatment coating is peeled off to expose a non-treated hydrophilic surface. As a result, no reaction with water takes place. Since no gelation due to a time period or a temperature occurs, the viscosity of the system can continuously be kept stably, thus providing a sunscreen cosmetic exhibiting a sustained favorable use feeling.

Composite Powder

A micro particle zinc oxide employed in the present invention is obtained generally by a French method or American method. A commercial micro particle zinc oxide having a mean particle size of 0.1 μm or less may for example be FINEX-25, FINEX-50, FINEX-75 (manufactured by Sakai Chemical Industry Co.), ZnO350 (manufactured by Sumitomo Osaka Cement Co.), ZINCOX SUPER-10, ZINCOX SUPER-20R, ZINCOX SUPER-30 (manufactured by Hakusui Chemical Industry Co.) and Z-COTE (manufactured by Sun Smart Co.).

Next, a method for producing a composite powder of the present invention is described below. A micro particle zinc oxide described above in an aqueous solution is kept as highly dispersed using a sand grinder mill or equivalent while adding sodium silicate and neutralizing, whereby forming a uniform coating of a silicic anhydride. Alternatively, a micro particle zinc oxide is highly dispersed in an organic solvent and then coated uniformly with a silicic anhydride using an alkoxysilane. Other production methods may also be employed in the present invention as far as a certain final amount of a silicic anhydride is coated. Preferably a silicic anhydride is coated in an amount of 5 to 30 wt %. An amount of 10 to 23 wt % is preferred especially. An amount less than 5 wt % results in a difficulty in coating a zinc oxide uniformly and causes the elution of a zinc ion which may lead to a reduced stability or a reduced ultraviolet rays protection effect. An amount exceeding 30 wt % causes a deteriorated use feeling such as a smoothlessness due to a silicic anhydride. Subsequently, various powder dispersing machines may be employed for the treatment with 3 to 12 wt % of a silicone to obtain an intended composite powder.

A silicone treatment agent may be silicone oils such as methyl hydrogen polysiloxane, dimethyl polysiloxane and methylphenyl polysiloxane, alkylsilanes such as methyl trimethoxysilane, ethyl trimethoxysilane, hexyl trimethoxysilane and octyl trimethoxysilane as well as fluoroalkylsilanes such as trifluoromethylethyl trimethoxysilane and heptadecafluorodecyl trimethoxysilane, which may be employed alone or in combination with each other.

A sunscreen cosmetic of the invention preferably contains 3 to 30 wt % of a composite powder. An amount of 10 to 23 wt % is particularly preferable since it exerts a well-balanced ultraviolet rays protection effect, transparency and use feeling. An amount less than 3 wt % gives no ultraviolet rays protection effect, while an amount exceeding 30 wt % results in an extremely poor transparency or use feeling.

Polyoxyalkylene-Modified Polysiloxane

A polyoxyalkylene-modified polysiloxane employed in the invention is represented by the general formulae [1], [2] and [3]:

In the general formulae [1], [2] and [3], R denotes a methyl group or partly a phenyl group, R denotes hydrogen or an alkyl group having 1 to 12 carbon atoms, p denotes an integer of 1 to 5, q denotes an integer of 2 to 3, and x, m and n denote mean numbers giving a polyoxyalkylene-modified organopolysiloxane which contains in its molecule 5 to 40 wt % of the polyoxyalkylene group and whose molecular weight is 2000 or more. Preferably, one or more of such polyoxyalkylene-modified organopolysiloxanes are incorporated in the present invention.

A polyoxyalkylene-modified polysiloxanes employed in the present invention can be incorporated in an amount of 0.5 to 7 wt % into a sunscreen cosmetic. An amount less than 5 wt % may lead to an insufficiently dispersed powder and a spotty aggregation. On the other hand, an amount exceeding 7 wt % gives a residual oil on skin, which leads to a stickiness, resulting in an extremely poor use feeling.

Dispersing Treatment

A media-agitating mill employed in the present invention for dispersing a powder in a wet condition may be batch type or continuous type bead mill, sand grinder mill, ball mill and the like. A high pressure dispersing machine may for example be a microfluidizer or a nanomizer. The material of a medium such as a bead, sand or ball employed in a media-agitating mill may for example be glass, alumina, zirconium, titanium, steal and the like, with zirconium being preferred particularly. The diameter of a medium usually is 0.3 to 2.0 mm, but 0.5 to 1.0 mm is preferred in the present invention. When a media-agitating mill or a high pressure dispersing machine is employed for dispersing a powder, it is preferable that a preceding step is provided wherein a primary treatment is performed using a dispersing machine having an ability of pulverizing a micro particle to some extent which is employed in an ordinary dispersing step such as a homomixer or a homogenizer. This procedure is desirable since such primary step for pulverizing a micro particle which is present initially as being aggregated serves to reduce the burden of the pulverizing and dispersing operations in a subsequent secondary step using a media-agitating mill or a high pressure dispersing machine, whereby allowing the micro particle to be pulverized and dispersed efficiently.

An example of a dispersing machine employed preferably in an inventive production method is described below with referring to a batch-type media-agitating mill. FIG. 1(A) shows a batch-type media-agitating mill.

A batch-type media-agitating mill is provided with basket 10 in tank 18 in combination with at least one internal tank stirrer 20 for both of preliminary mixing and dispersant fluidizing. Said basket 10 is provided with upper lid jacket 28, which is positioned with rod 16. On the side wall of basket 10, a number of small pores each consisting of a slit are provided. Basket 10 is provided with internal basket stirrer 14 for stirring the content of basket 10.

A starting material containing a powder is first mixed preliminarily by internal tank stirrer 20 to form a mixture, which is then introduced into basket 10 via an opening surrounding the rotation spindle of internal basket stirrer 14 fixed on the machine at the top of basket 10.

The inner view of basket 10 is shown in FIG. 1(B). Solid dispersing media (beads 22) are contained in basket 10, and internal basket stirrer 14 is provided with stirring pin disk 26 (or stirring disk) mounted vertically to the rotation spindle. Stirring pin disk 26 is provided with pin 24 for stirring.

The mixture once introduced into basket 10 is brought into contact with a stirring pin disk 26 which pulverizes and disperses an aggregated powder by means of solid dispersing media (beads 22) and then allowed to flow out via pores 12 each consisting of a number of slits provided on the side wall of basket 10.

An arrow mark of FIG. 1(A) shows an overall fluid route.

The dispersion thus allowed to flow out is then dispersed and fluidized by internal tank stirrer 20 and a part of it returns into basket 10 via the opening at the top of basket 10 to circulate through tank 18. It should be noted that the stirring part of internal tank stirrer 20 is located at a place which does not interfere the route of a flow into and out of basket 10. A media-agitating mill is a machine having a step capable of keeping a uniform dispersion of a powder in tank 18 as described above. An example of such dispersing machine employed preferably in the invention is one disclosed in JP-B-8-17930.

Figure 1:
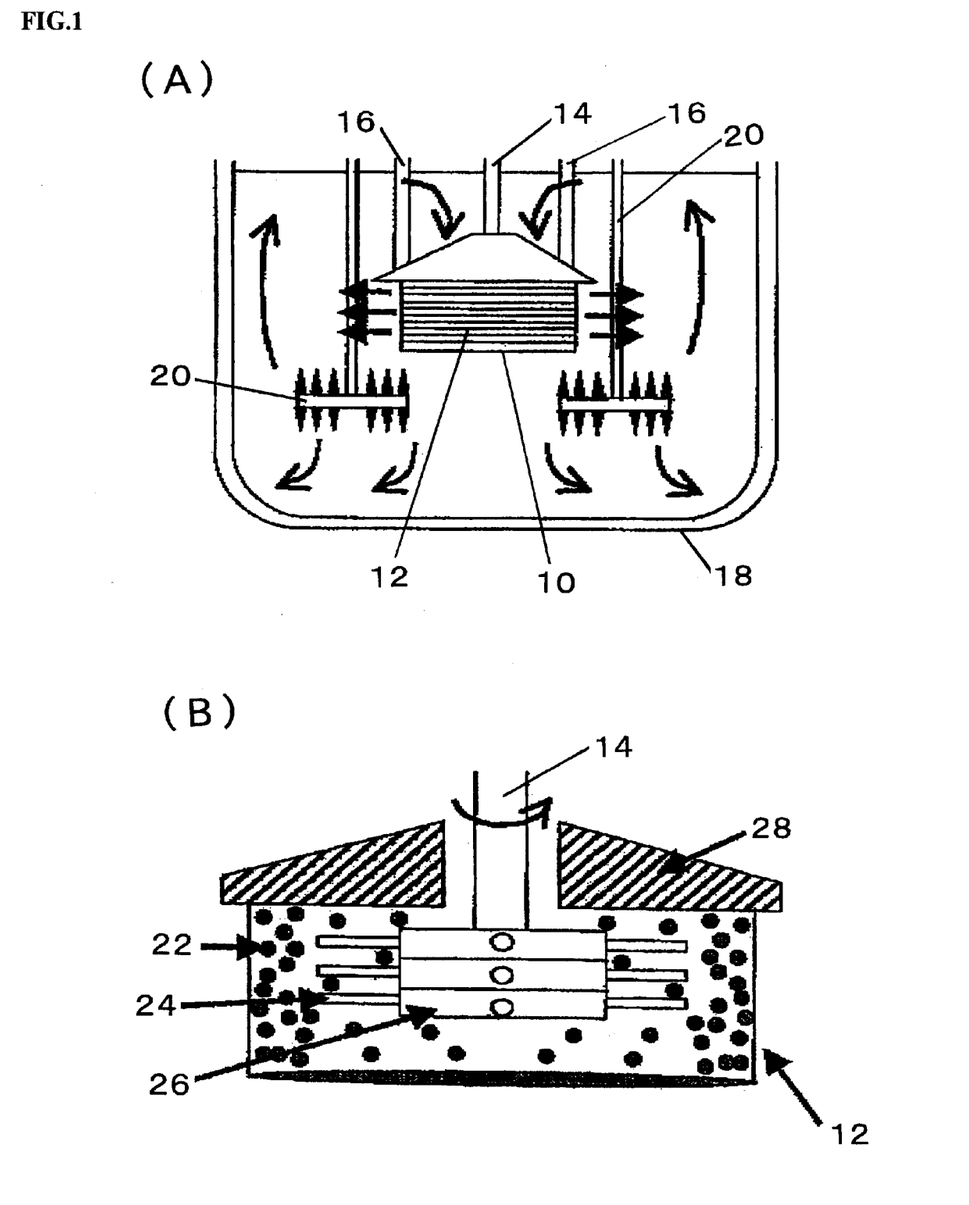
FIG. 1 shows an example of a media-agitating mill employed for preparing a sunscreen cosmetic.

A basket part filled with solid dispersing media (beads) which is provided in a media-agitating mill described above possesses on its side wall a number of small pores each consisting of a slit of a size which does not allow the solid dispersing media (beads) to go out of the basket, whereby preventing any beads from being contained in the resultant dispersion.

A media-agitating mill employed preferably in the invention is provided with small pores on the side wall of the basket filled with the beads. Accordingly, the rotation of a spindle exerts a centrifugal force, which localizes the beads on the side wall to establish a zone where the beads exist at a high density, through which a powder passes through, whereby raising the dispersion efficiency.

While an agitating machine for the purpose of both of a preliminary mixing and a dispersing fluidization may for example be an ordinary agitating machine employed preferably for producing a cosmetic, it is particularly preferable to use a Disper or a homogenizer fitted with a turbinal blade on the tip of a rotating rod.

Other Powders and Dispersant and Surface Treating Agent Therefor

A fatty acid, a fatty acid soap and a fatty acid ester as a dispersant or a surface treating agent for a powder employed in the invention may for example be a fatty acid such as palmitic acid, isostearic acid, stearic acid, lauric acid, myristic acid, behenic acid, oleic acid, rosinic acid and 12-hydroxystearic acid, a fatty acid soap such as aluminum stearate, calcium stearate, aluminum 12-hydroxystearate as well as dextrin fatty acid ester, cholesterol fatty acid ester, sucrose fatty acid ester, starch fatty acid ester and the like. Any of these materials may be employed alone or in combination with each other. Such material is present in an amount of 0.1 wt % or more for the purpose of exerting a function of a dispersant or a surface treating agent.

A sunscreen cosmetic of the present invention may also contain an inorganic powder such as titanium oxide, zinc oxide, iron oxide red, ion oxide yellow, iron oxide black, ultramarine, cerium oxide, talc, mica, sericite, kaolin, bentonite, clay, silicic acid, silicic anhydride, magnesium silicate, zinc stearate, fluorine-containing gold mica, synthetic talc, barium sulfate, magnesium sulfate, calcium sulfate, boron nitride, bismuth oxychloride, alumina, zirconium oxide, magnesium oxide, chromium oxide, calamine, magnesium carbonate or a combination thereof, and an organic powder such as silicone powder, silicone elastic powder, polyurethane powder, cellulose powder, nylon powder, PMMA powder, starch, polyethylene powder or a composite thereof, which may be employed alone or in combination with each other.

Other Ingredients

An oily ingredient in a sunscreen cosmetic of the present invention may for example be liquid paraffins, squalane, ester oils, diglycerides, triglycerides, perfluoropolyethers, vaseline, lanolin, ceresin, carnauba wax, paraffin waxes, fatty acids, polyhydric alcohols, silicone resins, fluorine resins, acrylic resins, vinyl pyrrolide and the like, which may be incorporated as an oily component alone or in combination with each other. A cosmetic of the present invention may also contain other additives such as pigments, pH modifiers, humectants, thickening agents, surfactants, dispersants, stabilizers, colorants, preservatives, antioxidants, ultraviolet rays absorbers and perfumes as long as it is not affected adversely by such additives.

The present invention is further described in the following Test examples and Examples. First, the following experiments were conducted to assess each surface treating agent for a micro particle zinc oxide having an ultraviolet rays protection effect.

EXPERIMENT 1

Peeling Strength of Surface Treating Agents for Various Surface-Treated Powders

The present inventors determined the peeling strength of a surface treating agent on respective surface-treated powder. The peeling strength of the surface treating agent on the surface-treated powder was calculated based on a % elution upon a Soxhlet extraction method (120° C. for 3 hours) using ethyl acetate as a solvent. Namely, a micro particle zinc oxide (specific surface area: about 80 $mm^2/g$) was coated with each surface-treating agent, and the resistance of the agent against a peeling was determined by the Soxhlet extraction method. The results of Test examples 1-1 to 1-5 were obtained. The results are shown in Table 1.

TABLE 1

| Surface-treating agent | | Elution (%: based on treating agent) |
|---|---|---|
| Silicic anhydride + Dimethyl silicone | (Test example 1-1) | 0.2 |
| Silicic anhydride + Methylhydrogen polysiloxane | (Test example 1-2) | 0.2 |
| Dimethyl silicone | (Test example 1-3) | 23.0 |
| Methylhydrogen polysiloxane | (Test example 1-4) | 1.5 |
| Fatty acid ester | (Test example 1-5) | 0.5 |

As evident from Table 1, the composite treated powder of Test example 1-1 obtained by coating a micro particle zinc oxide with a silicic anhydride followed by a surface treatment with dimethyl silicone exhibited a low elution of the treating agent, indicating that the surface treating agent was not readily peeled off. Also the composite treated powder of Test example 1-2 obtained by coating a micro particle zinc oxide with an silicic anhydride followed by a surface treatment with methylhydrogen polysiloxane exhibited a low elution of the treating agent, indicating that the surface treating agent was not readily peeled off. On the other hand, Test example 1-3 obtained by a surface treatment with dimethyl silicone without a coating with a silicic anhydride exhibited a high elution of the treating agent, indicating that the surface treating agent was readily peeled off. Each of Test examples 1-4 and 1-5 which were surface-treated with methylhydrogen polysiloxane and the fatty acid ester, respectively, exhibited a relatively low elution of the respective treating agent.

EXPERIMENT 2

Reaction Between Each Surface-Treated Powder and Fatty Acid

An ethanol solvent containing 2 wt % of oleic acid dissolved therein was combined with 10 wt % of a micro particle zinc oxide whose surface was treated respectively with an agent employed in Experiment 1 and then with glass beads in the amount of 50wt % based on the content volume, and subsequently the mixture was dispersed using a paint shaker for 1 hour and then examined for the state of the reaction between each surface-treated powder and the fatty acid in a beads dispersion system. Test examples 2-1 to 2-5 were obtained. The results are shown in Table 2.

TABLE 2

| Surface-treating agent | | Stability (Gelling behavior) |
|---|---|---|
| Silicic anhydride + Dimethyl silicone | (Test example 2-1) | No gelation |
| Silicic anhydride + Methylhydrogen polysiloxane | (Test example 2-2) | No gelation |
| Dimethyl silicone | (Test example 2-3) | Slight gelation |
| Methylhydrogen polysiloxane | (Test example 2-4) | Slight gelation |
| Fatty acid ester | (Test example 2-5) | Gelling |

As evident from Table 2, the composite treated powder of Test example 2-1 obtained by coating a micro particle zinc oxide with a silicic anhydride followed by a surface treatment with dimethyl silicone exhibited an excellent stability without undergoing any gelation. Also the treated composite powder of Test example 2-2 obtained by coating a micro particle zinc oxide with a silicic anhydride followed by a surface treatment with methylhydrogen polysiloxane exhibited an excellent stability without undergoing any gelation. On the other hand, each of Test examples 2-3, 2-4 and 2-5 obtained just by a surface treatment without any coating with a silicic anhydride underwent a gelation, thus revealing a poor stability.

Thus the results of Experiments 1 and 2 indicate that a powder coated with a silicic anhydride and then surface-treated with a silicone was resistant to the peeling off of the surface treating agent and did not react with a fatty acid even in a highly dispersed state. The inventors employed this composite powder treated with a silicic anhydride and a silicone to develop a sunscreen cosmetic.

Subsequently, the inventors prepared a sunscreen cosmetic to verify the practical performance. The practical performance was evaluated as described below. The ultraviolet rays protection effect was assessed using an in vitro SPF measurement system capable of determining SPF and PFA values at a high accuracy as described in JP-A-7-167781. The transparency of a formulation was assessed by applying a certain amount of the formulation over an artificial leather (2.0 mg/cm$^2$) and examining the color using CM-1000H (manufactured by Minolta Co.) with referring to a non-applied area, and then calculating a difference in the color (ΔE) (a lower ΔE corresponds to a higher transparency). The stability of a formulation was assessed after a time interval (at 50° C. for 1 month) by determining the viscosity after allowing the temperature to cool to 25° C. and by examining the change in the condition visually. An organoleptic assessment was also performed for the use feeling, and a visual assessment was performed for the transparency of a finished formulation on the skin. Each amount added was of % by weight.

Practical Performance Evaluation

Each of 20 female panelists applied a sample and evaluated the use feeling and the finish transparency.
<Evaluation>

| 17 Panelists or more judged as good. | ⊚ |
|---|---|
| 12 to 16 Panelists judged as good. | ○ |
| 9 to 11 Panelists judged as good. | Δ |
| 5 to 8 Panelists judged as good. | X |
| 4 Panelists or less judged as good. | X X |

EXPERIMENT 3

Investigation of Surfactant

The inventors investigated each surfactant which serves to disperse a micro particle zinc oxide coated with a silicic anhydride and treated with a silicone. Sunscreen cosmetics (W/O emulsion) of Test example 3-1 incorporating a polyoxyalkylene-modified polysiloxane, Test example 3-2 incorporating glycerin monostearate and Test example 3-3 incorporating sorbitan distearate were produced in accordance with the compositions indicated in the table shown below, and subjected to relevant tests and evaluations. Each composition was prepared by dispersing and emulsifying using a homogenizer. The results are shown in Table 3.

TABLE 3

| | Test ex. 3-1 | Test ex. 3-2 | Test ex. 3-3 |
|---|---|---|---|
| Cyclomethyl polysiloxane | 30 | 30 | 30 |
| Dimethylsilicone | 5 | 5 | 5 |
| Polyoxyalkylene-modified polysiloxane (polyoxyalkylene group: 20%, mean molecular weight: 6200) | 4 | — | — |
| Glyceryl monostearate (polyoxyethylene: 25 moles) | — | — | 4 |
| Sorbitan distearate | — | — | 4 |
| Silicone resin | 1 | 1 | 1 |
| Antioxidant | q.s. | q.s. | q.s. |
| Octyl methoxycinnamate | 3 | 3 | 3 |
| Monooleate | 1.5 | 1.5 | 1.5 |
| Cation-modified bentonite | 2 | 2 | 2 |
| Dimethyl silicone-treated silicic anhydride-coated micro particle zinc oxide (dimethyl silicone: 5 wt %, silicic anhydride 10 wt %, micro particle zinc oxide mean particle size 0.02 μm) | 17 | 17 | 17 |
| Calcium myristate-treated talc | 5 | 5 | 5 |
| PMMA spheric resin powder | 5 | 5 | 5 |
| Ion-exchanged water | to 100 | to 100 | to 100 |
| Glycerin | 4 | 4 | 4 |
| Polyethylene glycol | 1 | 1 | 1 |
| Preservative | q.s. | q.s. | q.s. |
| Stabilizer | q.s. | q.s. | q.s. |
| Perfume | q.s. | q.s. | q.s. |
| in vitro SPF value | 29.2 | 17.9 | 18.1 |
| in vitro PFA value | 7.2 | 5.4 | 4.9 |
| Transparency (ΔE) | 2.0 | 4.2 | 4.5 |
| Use feeling | ⊚ | Δ | Δ |
| Finish transparency | ⊚ | Δ | Δ |
| Viscosity (50° C.) | | | |
| Initial | 5700 | 4900 | 5100 |
| 1 month | 5900 | 5100 | 5500 |
| Stability (1 month) | ⊚ | Δ | Δ |

As evident from table 3, Test example 3-1 employing a certain polyoxyalkylene-modified polysiloxane according to the invention exhibited a better dispersibility of the particulate which leaded to a higher SPF value and a more excellent ultraviolet rays protection effect when compared with Test examples 3-2 and 3-3 employing other surfactants. Similarly, Test example 3-1 exhibited a higher PFA value, indicating that a higher preventive effect especially on UVA (320 to 400 nm) which is related more closely to a sunscreen effect among ultraviolet rays wavelengths. In addition, Test example 3-1 according to the invention had not only an excellent ultraviolet rays protection effect but also a higher transparency, as reflected by a lower ΔE, as well as an excellent finish transparency, showing a satisfactory use feeling. Furthermore, the sunscreen cosmetic of Test example 3-1 according to the invention underwent a reduced change in the viscosity over a time period, indicating an excellent stability. Thus, Test examples 3-2 and 3-3 employing prior arts revealed that a combination with a surfactant other than a poloxyalkylene-modified polysiloxane resulted in a poor dispersibility of the powder and a reduction in the ultraviolet rays protection effect and in the transparency.

Subsequently, we employed the compositions shown in Table 4 to examine the difference between the production methods. Test examples 3-1 and 3-4 were produced by dispersing and emulsifying using a homogenizer. Test examples 3-5 and 3-6 were produced by dispersing and emulsifying using a media-agitating mill. Test examples 3-4 and 3-6 contained no polyoxyalkylene-modified polysiloxane.

TABLE 4

|  | Test ex. 3-1 | Test ex. 3-4 | Test ex. 3-5 | Test ex. 3-6 |
|---|---|---|---|---|
| Cyclomethyl polysiloxane | 30 | 30 | 30 | 30 |
| Dimethylsilicone | 5 | 5 | 5 | 5 |
| Polyoxyalkylene-modified polysiloxane (polyoxyalkylene group: 20%, mean molecular weight: 6200) | 4 | — | 4 | — |
| Polyglyceryl triisostearate | — | 5 | — | 5 |
| Silicone resin | 1 | 1 | 1 | 1 |
| Antioxidant | q.s. | q.s. | q.s. | q.s. |
| Octyl methoxycinnamate | 3 | 3 | 3 | 3 |
| Monooleate | 1.5 | 1.5 | 1.5 | 1.5 |
| Cation-modified bentonite | 2 | 2 | 2 | 2 |
| Dimethyl silicone-treated silicic anhydride-coated micro particle zinc oxide (dimethyl silicone: 5 wt %, silicic anhydride: 10 wt %, micro particle zinc oxide mean particle size: 0.02 μm) | 17 | 17 | 17 | 17 |
| Calcium myristate-treated talc | 5 | 5 | 5 | 5 |
| PMMA spheric resin powder | 5 | 5 | 5 | 5 |
| Ion-exchanged water | to 100 | to 100 | to 100 | to 100 |
| Glycerin | 4 | 4 | 4 | 4 |
| Polyethylene glycol | 1 | 1 | 1 | 1 |
| Preservative | q.s. | q.s. | q.s. | q.s. |
| Stabilizer | q.s. | q.s. | q.s. | q.s. |
| Perfume | q.s. | q.s. | q.s. | q.s. |
| Use feeling | ⊚ | 66 | ⊚ | ○ |
| Finish transparency | ⊚ | 66 | ⊚ | ○ |
| Stability (1 month) | ⊚ | 66 | ⊚ | ○ |

As evident from Table 4, an excellent sunscreen cosmetic can be obtained by means of a preparation employing a media-agitating mill even when no polyoxyalkylene-modified polysiloxane is employed.

EXPERIMENT 4

Types of Polyoxyalkylene-Modified Polysiloxanes

The inventors investigated various polyoxyalkylene-modified polysiloxanes. Sunscreen cosmetics (W/O emulsions) of Test example 4-1 incorporating a certain polyoxyalkylene-modified polysiloxane according to the invention, Test example 4-2 incorporating a polyoxyalkylene-modified polysiloxane whose % polyoxyalkylene group was lower and Test example 4-3 incorporating a polyoxyalkylene-modified polysiloxane whose mean molecular weight was lower were produced in accordance with the compositions indicated in the table shown below, and subjected to relevant tests and evaluations. Each composition was prepared by dispersing and emulsifying using a homogenizer. The results are shown in Table 5.

TABLE 5

|  | Test ex. 4-1 | Test ex. 4-2 | Test ex. 4-3 |
|---|---|---|---|
| Cyclomethyl polysiloxane | 30 | 30 | 30 |
| Dimethylsilicone | 2 | 2 | 2 |

TABLE 5-continued

|  | Test ex. 4-1 | Test ex. 4-2 | Test ex. 4-3 |
|---|---|---|---|
| Polyoxyalkylene-modified polysiloxane (polyoxyalkylene group: 20%, mean molecular weight: 6200) | 5 | — | — |
| Polyoxyalkylene-modified polysiloxane (polyoxyalkylene group: 5%, mean molecular weight: 3000) | — | 5 | — |
| Polyoxyalkylene-modified polysiloxane (polyoxyalkylene group: 15%, mean molecular weight: 500) | — | — | 5 |
| Silicone resin | 1 | 1 | 1 |
| Antioxidant | q.s. | q.s. | q.s. |
| Octyl methoxycinnamate | 3 | 3 | 3 |
| 4-t-Butyl-4'-methoxybenzoylmethane | 1 | 1 | 1 |
| Isostearic acid | 1 | 1 | 1 |
| Silicone-treated barium sulfate | 3 | 3 | 3 |
| Cation-modified bentonite | 2 | 2 | 2 |
| Dimethyl silicone-treated silicic anhydride-coated micro particle zinc oxide (dimethyl silicone: 3 wt %, silicic anhydride: 22 wt %, micro particle zinc oxide mean particle size: 0.025 μm) | 18 | 18 | 18 |
| Talc | 5 | 5 | 5 |
| PMMA spheric resin powder | 5 | 5 | 5 |
| Ion-exchanged water | to 100 | to 100 | to 100 |
| Glycerin | 4 | 4 | 4 |
| Polyethylene glycol | 1 | 1 | 1 |
| Preservative | q.s. | q.s. | q.s. |
| Stabilizer | q.s. | q.s. | q.s. |
| Perfume | q.s. | q.s. | q.s. |
| in vitro SPF value | 27.4 | 21.4 | 22.2 |
| in vitro PFA value | 8.1 | 7.2 | 7.3 |
| Transparency (ΔE) | 1.8 | 4.6 | 4.9 |
| Use feeling | ⊚ | ○ | ○ |
| Finish transparency | ⊚ | Δ | Δ |
| Viscosity (50° C.) |  |  |  |
| Initial | 5600 | 5200 | 4700 |
| 1 month | 5900 | 5900 | 5400 |
| Stability (1 month) | ⊚ | X | X |

As evident from table 5, Test example 4-1 employing a certain polyoxyalkylene-modified polysiloxane according to the invention exhibited a higher SPF value when compared with Test examples 4-2 and 4-3 employing those other than a certain polyoxyalkylene-modified polysiloxane, indicating a more excellent ultraviolet rays protection effect. Similarly, Test example 4-1 exhibited a higher PFA value, indicating a higher preventive effect especially on UVA (320 to 400 nm) which is related more closely to a sunscreen effect among ultraviolet rays wavelengths. In addition, Test example 4-1 according to the invention had not only an excellent ultraviolet rays protection effect but also a higher transparency, as reflected by a lower ΔA, as well as an excellent finish transparency, showing a satisfactory use feeling. Furthermore, the sunscreen cosmetic of Test example 4-1 according to the invention underwent a reduced change in the viscosity over a time period, indicating an excellent stability. Thus, Test examples 4-2 and 4-3 revealed that a poor dispersibility and a reduced emulsion stability were attributable to the difference in the % polyoxyalkylene group and in the molecular weight of the polyoxyalkylene-modified polysiloxane.

Subsequently, we employed the compositions shown in Table 6 to examine the difference between the production methods. Test examples 4-1 and 4-4 were produced by dispersing and emulsifying using a homogenizer. Test examples 4-5 and 4-6 were produced by dispersing and emulsifying using a media-agitating mill. Test examples 4-4 and 4-6 contained no polyoxyalkylene-modified polysiloxane.

TABLE 6

|  | Test ex. 4-1 | Test ex. 4-4 | Test ex. 4-5 | Test ex. 4-6 |
|---|---|---|---|---|
| Cyclomethyl polysiloxane | 30 | 30 | 30 | 30 |
| Dimethylsilicone | 2 | 2 | 2 | 2 |
| Polyoxyalkylene-modified polysiloxane (polyoxyalkylene group: 20%, mean molecular weight: 6200) | 5 | — | 5 | — |
| Polyglyceryl triisostearate | — | 5 | — | 5 |
| Silicone resin | 1 | 1 | 1 | 1 |
| Antioxidant | q.s. | q.s. | q.s. | q.s. |
| Octyl methoxycinnamate | 3 | 3 | 3 | 3 |
| 4-t-Butyl-4'-methoxybenzoyl-methane | 1 | 1 | 1 | 1 |
| Isostearic acid | 1 | 1 | 1 | 1 |
| Silicone-treated barium sulfate | 3 | 3 | 3 | 3 |
| Cation-modified bentonite | 2 | 2 | 2 | 2 |
| Dimethyl silicone-treated silicic anhydride-coated micro particle zinc oxide (dimethyl silicone: 3 wt %, silicic anhydride: 22 wt %, micro particle zinc oxide mean particle size: 0.025 μm) | 18 | 18 | 18 | 18 |
| Talc | 5 | 5 | 5 | 5 |
| PMMA spheric resin powder | 5 | 5 | 5 | 5 |
| Ion-exchanged water | to 100 | to 100 | to 100 | to 100 |
| Glycerin | 4 | 4 | 4 | 4 |
| Polyethylene glycol | 1 | 1 | 1 | 1 |
| Preservative | q.s. | q.s. | q.s. | q.s. |
| Stabilizer | q.s. | q.s. | q.s. | q.s. |
| Perfume | q.s. | q.s. | q.s. | q.s. |
| Use feeling | ⊚ | Δ | ⊚ | ○ |
| Finish transparency; | ⊚ | Δ | ⊚ | ○ |
| Stability (1 month) | ⊚ | Δ | ⊚ | ○ |

As evident from Table 6, an excellent sunscreen cosmetic can be obtained by means of a preparation employing a media-agitating mill even when no polyoxyalkylene-modified polysiloxane is employed.

EXPERIMENT 5

Types of Surface-Treated Powders

The inventors prepared and investigated the sunscreen cosmetics containing various surface-treated micro particle zinc oxides. Sunscreen cosmetics (W/O emulsions) of Test example 5-1 employing a coating with a silicic anhydride and a silicone treatment according to the invention, Test example 5-2 employing only a silicone treatment and Test example 5-3 employing only a myristic acid treatment were produced in accordance with the compositions indicated in the table shown below, and subjected to relevant tests and evaluations. Each composition was prepared by dispersing and emulsifying using a homogenizer.

The results are shown in Table 7.

TABLE 7

|  | Test ex. 5-1 | Test ex. 5-2 | Test ex. 5-3 |
|---|---|---|---|
| Cyclomethyl polysiloxane | 38 | 38 | 38 |
| Dimethylsilicone | 3 | 3 | 3 |
| Octyl methoxycinnamate | 5 | 5 | 5 |
| Polyoxyalkylene-modified polysiloxane (polyoxyalkylene group: 15%, mean molecular weight: 6000) | 3 | 3 | 3 |
| Silicone resin | 2 | 2 | 2 |
| Bentonite | 1 | 1 | 1 |
| Antioxidant | q.s. | q.s. | q.s. |
| Dimethyl silicone-treated silicic anhydride-coated micro particle zinc oxide (dimethyl silicone: 3 wt %, silicic anhydride: 20 wt %, micro particle zinc oxide mean particle size: 0.03 μm) | 15 | — | — |
| Dimethyl silicone-treated micro particle zinc oxide (dimethyl silicone: 7 wt %, micro particle zinc oxide mean particle size: 0.03 μm) | — | 15 | — |
| Myristic acid-treated micro particle zinc oxide (myristic acid: 12 wt %, micro particle zinc oxide mean particle size: 0.03 μm) | — | — | 15 |
| Aluminum stearate-treated micro particle titanium oxide | 4 | 4 | 4 |
| Nylon powder | 5 | 5 | 5 |
| Ion-exchanged water | to 100 | to 100 | to 100 |
| Glycerin | 5 | 5 | 5 |
| Dipropylene glycol | 5 | 5 | 5 |
| Preservative | q.s. | q.s. | q.s. |
| Stabilizer | q.s. | q.s. | q.s. |
| Perfume | q.s. | q.s. | q.s. |
| in vitro SPF value | 38.3 | 28.7 | 29.2 |
| in vitro PFA value | 9.8 | 6.4 | 7.2 |
| Transparency (ΔE) | 3.2 | 5.8 | 6.6 |
| Use feeling | ⊚ | Δ | ○ |
| Finish transparency | ○ | Δ | X |
| Viscosity (50° C.) |  |  |  |
| Initial | 4800 | 5200 | 4500 |
| 1 month | 4900 | 7400 | 7700 |
| Stability (1 month) | ⊚ | Δ | Δ |

As evident from table 7, Test example 5-1 employing a micro particle zinc oxide coated with a silicic anhydride and surface-treated with a silicone according to the invention exhibited a higher SPF value when compared with Test examples 5-2 and 5-3 employing micro particle zinc oxides which were not treated similarly, indicating a more excellent ultraviolet rays protection effect. Similarly, Test example 5-1 exhibited a higher PFA value, indicating a higher preventive effect especially on UVA (320 to 400 nm) which is related more closely to a sunscreen effect among ultraviolet rays wavelengths. In addition, Test example 5-1 according to the invention had not only an excellent ultraviolet rays protection effect but also a higher transparency, as reflected by a lower ΔE, as well as an excellent finish transparency, showing a satisfactory use feeling. Furthermore, the sunscreen cosmetic of Test example 5-1 according to the invention underwent a reduced change in the viscosity over a time period, indicating an excellent stability. Thus, the composite surface treatment of the micro particle zinc oxide of each of Test examples 5-2 and 5-3 according to prior arts revealed to give a poor system stability and a reduced ultraviolet rays protection effect.

Subsequently, the inventors employed the compositions shown in Table 8 to examine the difference between the production methods. Test examples 5-1 and 5-4 were produced by dispersing and emulsifying using a homogenizer. Test examples 5-5 and 5-6 were produced by dispersing and emulsifying using a media-agitating mill. Test examples 5-4 and 5-6 contained no polyoxyalkylene-modified polysiloxane.

TABLE 8

|  | Test ex. 5-1 | Test ex. 5-4 | Test ex. 5-5 | Test ex. 5-6 |
|---|---|---|---|---|
| Cyclomethyl polysiloxane | 38 | 38 | 38 | 38 |
| Dimethylsilicone | 3 | 3 | 3 | 3 |
| Octyl methoxycinnamate | 5 | 5 | 5 | 5 |
| Polyoxyalkylene-modified polysiloxane (polyoxyalkylene group: 15%, mean molecular weight: 6000) | 3 | — | 3 | — |
| Polyglyceryl triisostearate | — | 4 | — | 4 |
| Silicone resin | 2 | 2 | 2 | 2 |
| Bentonite | 1 | 1 | 1 | 1 |
| Antioxidant | q.s. | q.s. | q.s. | q.s. |
| Dimethyl silicone-treated silicic anhydride-coated micro particle zinc oxide (dimethyl silicone: 3 wt %, silicic anhydride: 20 wt %, micro particle zinc oxide mean particle size: 0.03 μm) | 15 | 15 | 15 | 15 |
| Aluminum stearate-treated micro particle titanium oxide | 4 | 4 | 4 | 4 |
| Nylon powder | 5 | 5 | 5 | 5 |
| Ion-exchanged water | to 100 | to 100 | to 100 | to 100 |
| Glycerin | 5 | 5 | 5 | 5 |
| Dipropylene glycol | 5 | 5 | 5 | 5 |
| Preservative | q.s. | q.s. | q.s. | q.s. |
| Stabilizer | q.s. | q.s. | q.s. | q.s. |
| Perfume | q.s. | q.s. | q.s. | q.s. |
| Use feeling | ⊚ | Δ | ⊚ | ○ |
| Finish transparency | ○ | Δ | ⊚ | ○ |
| Stability (1 month) | ⊚ | Δ | ⊚ | ○ |

As evident from Table 8, an excellent sunscreen cosmetic can be obtained by means of a preparation employing a media-agitating mill even when no polyoxyalkylene-modified polysiloxane is employed.

EXPERIMENT 6

Composite Powder Content

The inventors investigated a varying amount of a composite powder obtained by coating a micro particle zinc oxide with a silicic anhydride followed by a surface treatment with a silicone. Among the constituents of Test example 3-1, the amount of a composite powder obtained by coating a micro particle zinc oxide with a silicic anhydride followed by a surface treatment with a silicone was changed to prepare the sunscreen cosmetics shown in Table 9, which were examined for the ultraviolet rays protection effect, the use feeling, the finish transparency and the stability. Each composition was prepared by dispersing and emulsifying using a homogenizer. The experiment and the assessment were similar to those described above, except for the ultraviolet rays protection effect which was in accordance with the following evaluation criteria.

<Ultraviolet Rays Protection Effect>

A formulation which did not contain a composite powder obtained by coating a micro particle zinc oxide with a silicic anhydride followed by a surface treatment with a silicone was prepared and compared with a composition of Test example with regard to the in vitro SPF value and the in vitro PFA value. The evaluation criteria are described below.

⊙: Increase in in vitro SPF by 8 or more and in vitro PFA by 5 or more
○: Increase in in vitro SPF by 4 or more and less than 8 and in vitro PFA by 2 or more and less than 5
Δ: Increase in in vitro SPF by 1 or more and less than 4 and in vitro PFA by 1 or more and less than 2
×: No increase in in vitro SPF or in vitro PFA

TABLE 9

|  | Test ex. 6-1 | Test ex. 6-2 | Test ex. 6-3 | Test ex. 6-4 |
|---|---|---|---|---|
| Cyclomethyl polysiloxane | 30 | 30 | 30 | 30 |
| Dimethylsilicone | 5 | 5 | 5 | 5 |
| Polyoxyalkylene-modified polysiloxane polyoxyalkylene group: 20%, mean molecular weight: 6200) | 4 | 4 | 4 | 4 |
| Silicone resin | 1 | 1 | 1 | 1 |
| Antioxidant | q.s. | q.s. | q.s. | q.s. |
| Octyl methoxycinnamate | 3 | 3 | 3 | 3 |
| Monooleate | 1.5 | 1.5 | 1.5 | 1.5 |
| Cation-modified bentonite | 2 | 2 | 2 | 2 |
| Dimethyl silicone-treated silicic anhydride-coated micro particle zinc oxide (dimethyl silicone: 5 wt %, silicic anhydride: 10 wt %, micro particle zinc oxide mean particle size: 0.02 μm) | 3 | 10 | 23 | 30 |
| Calcium myristate-treated talc | 5 | 5 | 5 | 5 |
| PMMA spheric resin powder | 5 | 5 | 5 | 5 |
| Ion-exchanged water | to 100 | to 100 | to 100 | to 100 |
| Glycerin | 4 | 4 | 4 | 4 |
| Polyethylene glycol | 1 | 1 | 1 | 1 |
| Preservative | q.s. | q.s. | q.s. | q.s. |
| Stabilizer | q.s. | q.s. | q.s. | q.s. |
| Perfume | q.s. | q.s. | q.s. | q.s. |
| Ultraviolet rays protection effect | Δ | ○ | ⊚ | ⊚ |
| Use feeling | ⊚ | ⊚ | ○ | Δ |
| Finish transparency | ⊚ | ⊚ | ○ | Δ |
| Stability (1 month) | ⊚ | ⊚ | ⊚ | ○ |

As evident from Table 9, the composite powder obtained by coating a micro particle zinc oxide with a silicic anhydride followed by a surface treatment with a silicone was added preferably in an amount of 3 to 30 wt %.

EXPERIMENT 7

Polyoxyalkylene-Modified Polysiloxane Content

We then made an investigation while focusing on the amount of the polyoxyalkylene-modified polysiloxane. Among the constituents of Test example 5-1, the polyoxyalkylene-modified polysiloxane content was changed to prepare the sunscreen cosmetics shown in the following table. Then the ultraviolet rays protection effect, the use feeling, the finish transparency and the stability were investigated. Each composition was prepared by dispersing and emulsifying using a homogenizer. The experiment and the assessment were similar to those described above. The results are shown in Table 10.

TABLE 10

|  | Test ex. 7-1 | Test ex. 7-2 | Test ex. 7-3 |
|---|---|---|---|
| Cyclomethyl polysiloxane | 38 | 38 | 38 |
| Dimethylsilicone | 3 | 3 | 3 |
| Octyl methoxycinnamate | 5 | 5 | 5 |
| Polyoxyalkylene-modified polysiloxane polyoxyalkylene group: 15%, mean molecular weight: 6000) | 0.5 | 3 | 7 |
| Silicone resin | 2 | 2 | 2 |
| Bentonite | 1 | 1 | 1 |
| Antioxidant | q.s. | q.s. | q.s. |

TABLE 10-continued

|  | Test ex. 7-1 | Test ex. 7-2 | Test ex. 7-3 |
|---|---|---|---|
| Dimethyl silicone-treated silicic anhydride-coated micro particle zinc oxide (dimethyl silicone: 3 wt %, silicic anhydride: 20 wt %, micro particle zinc oxide mean particle size: 0.03 µm) | 15 | 15 | 15 |
| Aluminum stearate-treated micro particle titanium oxide | 4 | 4 | 4 |
| Nylon powder | 5 | 5 | 5 |
| Ion-exchanged water | to 100 | to 100 | to 100 |
| Glycerin | 5 | 5 | 5 |
| Dipropylene glycol | 5 | 5 | 5 |
| Preservative | q.s. | q.s. | q.s. |
| Stabilizer | q.s. | q.s. | q.s. |
| Perfume | q.s. | q.s. | q.s. |
| Ultraviolet rays protection effect | ◯ | ◎ | ◎ |
| Use feeling | ◎ | ◎ | ◯ |
| Finish transparency | ◯ | ◎ | ◎ |
| Stability (1 month) | ◯ | ◎ | ◎ |

As evident from Table 10, the polyoxyalkylene-modified polysiloxane according to the invention was added preferably in an amount of 0.5 to 7 wt %.

Further explains of the present invention by examples and comparative examples are described below.

EXAMPLE 1

W/O Emulsions

The inventors prepared and investigated the W/O emulsions shown in Table 11. Example 1-1 was obtained by mixing the oil phase components in a formulation with the powder components, pulverizing and dispersing in a media-agitating mill and then adding the aqueous phase components to form an emulsion. Example 1-2 was prepared using the same formulation by dispersing and emulsifying using a homogenizer as in an ordinary manufacturing process. Comparative examples 1-1 and 1-2 were produced using different surface-treated zinc oxides in a process employing a media-agitating mill.

TABLE 11

|  | Ex. 1-1 | Ex. 1-2 | Comp. ex.1-1 | Comp. ex.1-2 |
|---|---|---|---|---|
| Cyclomethyl polysiloxane | 30 | 30 | 30 | 30 |
| Dimethyl silicone | 3 | 3 | 3 | 3 |
| Glyceryl tri-2-ethylhexanoate | 5 | 5 | 5 | 5 |
| Polyoxyalkylene-modified polysiloxane polyoxyalkylene group: 15%, mean molecular weight: 6000) | 3 | 3 | 3 | 3 |
| Sorbitan sesquiisostearate | 1 | 1 | 1 | 1 |
| Isostearic acid | 1 | 1 | 1 | 1 |
| Bentonite | 1 | 1 | 1 | 1 |
| Antioxidant | q.s. | q.s. | q.s. | q.s. |
| Dimethyl silicone-treated silicic anhydride-coated zinc oxide (dimethyl silicone: 3 wt %, silicic anhydride: 20 wt %, micro particle zinc oxide mean particle size: 0.03 µm) | 15 | 15 | — | — |
| Dimethyl silicone-treated micro particle zinc oxide (dimethyl silicone: 7 wt %, micro particle zinc oxide mean particle size: 0.03 µm) | — | — | 15 | — |
| Myristic acid-treated micro particle zinc oxide (myristic acid: 12 wt %, micro particle zinc oxide mean particle size: 0.03 µm) | — | — | — | 15 |
| Aluminum stearate-treated micro particle titanium oxide | 5 | 5 | 5 | 5 |
| Nylon powder | 5 | 5 | 5 | 5 |
| Ion-exchanged water | to 100 | to 100 | to 100 | to 100 |
| Glycerin | 5 | 5 | 5 | 5 |
| Dipropylene glycol | 5 | 5 | 5 | 5 |
| Preservative | q.s. | q.s. | q.s. | q.s. |
| Stabilizer | q.s. | q.s. | q.s. | q.s. |
| Perfume | q.s. | q.s. | q.s. | q.s. |
| in vitro SPF value | 41.5 | 35.8 | 29.7 | 31.2 |
| in vitro SPA value | 11.2 | 9.8 | 7.4 | 7.8 |
| Transparency (ΔE) | 4.2 | 4.9 | 6.8 | 7.6 |
| Use feeling | ◎ | ◯ | Δ | ◯ |
| Finish transparency | ◎ | ◯ | Δ | Δ |
| Viscosity (50° C.) Initial | 18000 | 14500 | 16000 | 13800 |
| 1 month | 16800 | 13260 | 17000 | 45000 |
| Stability (1 month) | ◎ | ◎ | ◯ | X |

As evident from Table 11, each of Comparative examples 1-1 and 1-2 incorporating a micro particle zinc oxide which was not coated with a silicic anhydride exhibited a poorly stable viscosity as well as poor use feeling and finish transparency. On the contrary, each of Examples 1-1 and 1-2 incorporating a micro particle zinc oxide which was coated with a silicic anhydride and then treated with a silicone exhibited a stable viscosity and excellent use feeling and finish transparency. In addition, Examples 1-1 and 1-2 showed excellent results also in terms of the transparency (ΔE), the in vitro SPF and the in vitro SPA. When comparing Example 1-1 with Example 1-2, Example 1-1 employing a media-agitating mill showed a higher ultraviolet rays protection effect and a more satisfactory use feeling than Example 1-2 employing an ordinary homogenizer.

EXAMPLE 2

W/O) Emulsions

The inventors prepared and investigated the W/O emulsions shown in Table 12. Example 2-1 was obtained by mixing the oil phase components in a formulation with the powder components, pulverizing and dispersing in a media-agitating mill and then adding the aqueous phase components to form an emulsion. Example 2-2 was prepared using the same formulation by dispersing and emulsifying using a homogenizer as in an ordinary manufacturing process. Comparative examples 2-1 and 2-2 were produced using different surface-treated zinc oxides in a process employing a media-agitating mill.

TABLE 12

|  | Ex. 2-1 | Ex. 2-2 | Comp. ex.2-1 | Comp. ex.2-2 |
|---|---|---|---|---|
| Cyclomethyl polysiloxane | 30 | 30 | 30 | 30 |
| Dimethyl silicone | 3 | 3 | 3 | 3 |
| Polyoxyalkylene-modified polysiloxane polyoxyalkylene group: 20%, mean molecular weight: 6200) | 3 | 3 | 3 | 3 |
| Silicone resin | 2 | 2 | 2 | 2 |

TABLE 12-continued

|  | Ex. 2-1 | Ex. 2-2 | Comp. ex.2-1 | Comp. ex.2-2 |
|---|---|---|---|---|
| Antioxidant | q.s. | q.s. | q.s. | q.s. |
| Octyl mehtoxycinnamate | 1 | 1 | 1 | 1 |
| 44-Butyl-4'-methoxybenzoylmethane | 1 | 1 | 1 | 1 |
| Isostearic acid | 1 | 1 | 1 | 1 |
| Cation-modified bentonite | 1 | 1 | 1 | 1 |
| Methylhydrogen polysiloxane-treated silicic anhydride-coated zinc oxide (methylhydrogen polysiloxane: 3 wt %, silicic anhydride: 22 wt %, micro particle zinc oxide mean particle size: 0.025 μm) | 18 | 18 | — | — |
| Methylhydrogen polysiloxane-treated micro particle zinc oxide (methylhydrogen polysiloxane: 7 wt %, micro particle zinc oxide mean particle size: 0.03 μm) | — | — | 18 | — |
| Myristic acid-treated micro particle zinc oxide (myristic acid: 12 wt %, micro particle zinc oxide mean particle size: 0.03 μm) | — | — | — | 18 |
| Calcium myristate-treated talc | 5 | 5 | 5 | 5 |
| PMMA spheric resin powder | 5 | 5 | 5 | 5 |
| Ion-exchanged water | to 100 | to 100 | to 100 | to 100 |
| Glycerin | 4 | 4 | 4 | 4 |
| Polyethylene glycol | 1 | 1 | 1 | 1 |
| Preservative | q.s. | q.s. | q.s. | q.s. |
| Stabilizer | q.s. | q.s. | q.s. | q.s. |
| Perfume | q.s. | q.s. | q.s. | q.s. |
| in vitro SPF value | 42.5 | 37.4 | 34.4 | 35.2 |
| in vitro SPA value | 9.2 | 8.1 | 7.2 | 7.8 |
| Transparency (ΔE) | 1.6 | 2.2 | 4.6 | 4.9 |
| Use feeling | ⊚ | ○ | ○ | ○ |
| Finish transparency | ⊚ | ○ | Δ | Δ |
| Viscosity (50° C.) Initial | 5800 | 4800 | 4500 | 4700 |
| 1 month | 5500 | 4900 | 5400 | 6300 |
| Stability (1 month) | ⊚ | ⊚ | Δ | X |

As evident from Table 12, each of Comparative examples 2-1 and 2-2 incorporating a micro particle zinc oxide which was not coated with a silicic anhydride exhibited a poor ultraviolet rays protection effect, a poorly stable viscosity and a poor finish transparency. On the contrary, each of Examples 2-1 and 2-2 incorporating a micro particle zinc oxide which was coated with a silicic anhydride and then treated with a silicone exhibited a stable viscosity and excellent use feeling and finish transparency. In addition, Examples 2-1 and 2-2 showed excellent results also in terms of the transparency (ΔE), the in vitro SPF and the in vitro SPA. When comparing Example 2-1 with Example 2-2, Example 2-1 employing a media-agitating mill showed a higher ultraviolet rays protection effect and a more satisfactory use feeling than Example 2-2 employing an ordinary homogenizer.

EXAMPLE 3

Oily Compositions

The inventors prepared and investigated the oily compositions shown in Table 13. Example 3-1 was obtained by mixing the all components in a formulation and pulverizing and dispersing in a media-agitating mill. Example 3-2 was prepared using the same formulation by dispersing using a homogenizer as in an ordinary manufacturing process. Comparative examples 3-1 and 3-2 were produced using different surface-treated zinc oxides in a process employing a media-agitating mill. The results are shown in Table 13.

TABLE 13

|  | Ex. 3-1 | Ex. 3-2 | Comp. ex.3-1 | Comp. ex.3-2 |
|---|---|---|---|---|
| Cyclomethyl polysiloxane | to 100 | to 100 | to 100 | to 100 |
| Dimethyl silicone | 5 | 5 | 5 | 5 |
| Alcohol | 8 | 8 | 8 | 8 |
| Polyoxyalkylene-modified polysiloxane polyoxyalkylene group: 20%, mean molecular weight: 6200) | 3 | 3 | 3 | 3 |
| Sorbitan sesquiisostearate | 1 | 1 | 1 | 1 |
| Silicone resin | 8 | 8 | 8 | 8 |
| Antioxidant | q.s. | q.s. | q.s. | q.s |
| Octyl methoxycinnamate | 3 | 3 | 3 | 3 |
| Cation-modified bentonite | 0.5 | 0.5 | 0.5 | 0.5 |
| Dimethyl silicone-treated silicic anhydride-coated zinc oxide (dimethyl silicone: 5 wt %, silicic anhydride: 10 wt %, micro particle zinc oxide mean particle size: 0.02 μm) | 12 | 12 | — | — |
| Dimethyl silicone-treated micro particle zinc oxide (dimethyl silicone: 7 wt %, micro particle zinc oxide mean particle size: 0.03 μm) | — | — | 12 | — |
| Myristic acid-treated micro particle zinc oxide (myristic acid: 12 wt %, micro particle zinc oxide mean particle size: 0.03 μm) | — | — | — | 12 |
| Aluminum stearate-treated micro particle titanium oxide | 3 | 3 | 3 | 3 |
| PMMA spheric resin powder | 5 | 5 | 5 | 5 |
| Silicone-treated talc | 15 | 15 | 15 | 15 |
| Perfume | q.s. | q.s. | q.s. | q.s. |
| in vitro SPF value | 42.5 | 37.4 | 34.4 | 35.2 |
| in vitro SPA value | 9.2 | 8.1 | 7.2 | 7.8 |
| Transparency (ΔE) | 1.6 | 2.2 | 4.6 | 4.9 |
| Use feeling | ⊚ | ○ | ○ | Δ |
| Finish transparency | ⊚ | ○ | ○ | Δ |
| Viscosity (50° C.) Initial | 3800 | 2500 | 2900 | 3200 |
| 1 month | 3400 | 2800 | 2350 | 6900 |
| Stability (1 month) | ⊚ | ⊚ | ○ | X |

As evident from Table 13, each of Comparatives example 3-1 and 3-2 incorporating a micro particle zinc oxide which was not coated with a silicic anhydride exhibited a poor ultraviolet rays protection effect, combined with a poorly stable viscosity especially in Comparative example 3-2, as well as poor use feeling and finish transparency. On the contrary, each of Examples 3-1 and 3-2 incorporating a micro particle zinc oxide which was coated with a silicic anhydride and then treated with a silicone exhibited a stable viscosity and excellent use feeling and finish transparency. In addition, Examples 3-1 and 3-2 showed excellent results especially in terms of the transparency (ΔE), the in vitro SPF and the in vitro SPA. When comparing Example 3-1 with Example 3-2, Example 3-1 employing a media-agitating mill showed a higher ultraviolet rays protection effect and a more satisfactory use feeling than Example 3-2 employing an ordinary homogenizer.

Further examples of the invention are described below.

Example 4: Powdery foundation (usable also with water)

| Silicone-treated sericite | 18 |
|---|---|
| Silicone-treated mica | to 100 |

-continued

| | |
|---|---|
| Silicone-treated talc | 15 |
| Dimethyl silicone-treated silicic anhydride-coated zinc oxide | 6 |
| Silicone-treated titanium oxide | 8 |
| Aluminum stearate-treated micro particle titanium oxide | 6 |
| Silicone-treated iron oxide red | 1.2 |
| Silicone-treated iron oxide yellow | 2.5 |
| Silicone-treated iron oxide black | 0.9 |
| Polyurethane powder | 6 |
| Parabene | q.s. |
| Dimethyl polysiloxane | 4 |
| Methylphenyl polysiloxane | 3 |
| Octyl methoxycinnamate | 3 |
| Polyoxyalkylene-modified polysiloxane | 2 |
| (polyoxyalkylene group: 15%, mean molecular weight: 6000) | |
| Antioxidant | q.s. |
| Perfume | q.s. |

[Manufacturing method]
The oily components and the powder components in the formulation shown above were mixed together with other components, and pulverized and dispersed using a media- agitating mill to obtain a powdery foundation.

Example 5: Face powder (white powder)

| | |
|---|---|
| Talc | to 100 |
| Mica | 25 |
| Dimethyl silicone-treated silicic anhydride-coated zinc oxide | 5 |
| Micro particle titanium oxide | 3 |
| Spheric silicone powder | 1 |
| Vaseline | 1 |
| Methylphenyl polysiloxane | 3 |
| Ester oil | 1 |
| Polyoxyalkylene-modified polysiloxane | 0.5 |
| (polyoxyalkylene group: 15%, mean molecular weight: 6200) | |
| Parabene | q.s. |
| Antioxidant | q.s. |
| Perfume | q.s. |

[Manufacturing method]
The all components in the formulation shown above were mixed, and pulverized and dispersed using a media-agitating mill to obtain a face powder.

Example 6: Emulsified cream foundation

| | |
|---|---|
| Talc | 14 |
| Sericite | 10 |
| Iron oxide red | 0.3 |
| Iron oxide yellow | 1.2 |
| Iron oxide black | 0.6 |
| Spheric polyethylene powder | 6 |
| Dimethyl silicone-treated silicic anhydride-coated zinc oxide | 3 |
| Dimethyl polysiloxane(0.006Pa·S) | 10 |
| Olive oil | 10 |
| Stearic acid | 2 |
| Polyoxyalkylene-modified polysiloxane | 0.5 |
| (polyoxyalkylene group: 15%, mean molecular weight: 6000) | |
| Glyceryl monostearate | 2 |
| POE (40) sorbitan monostearate | 2 |
| Glycerin | 5 |
| Triethanolamine | 0.8 |
| pH modifier | q.s. |
| Preservative | q.s. |
| Ion-exchanged water | q.s. |

[Manufacturing method]
The oily components and the powder components in the formulation shown above were mixed, and pulverized and dispersed using a media-agitating mill. The composition thus obtained was then combined with the aqueous phase components and emulsified to obtain an emulsified cream foundation.

Example 7: Emulsified liquid foundation (W/O)

| | |
|---|---|
| Silicone-treated mica | 14 |
| Silicone-treated sericite | 11 |
| Dimethyl silicone-treated silicic anhydride-coated zinc oxide | 8 |
| Spheric PMMA powder | 4 |
| Cyclomethyl polysiloxane | to 100 |
| Dimethyl polysiloxane | 4 |
| Squalane | 3 |
| Polyoxyalkylene-modified polysiloxane | 2 |
| (polyoxyalkylene group: 20%, mean molecular weight: 6000) | |
| Sorbitan sesquiisostearate | 1 |

-continued

| | |
|---|---|
| Dispersing aid | q.s. |
| Dipropylene glycol | 2 |
| Ion-exchanged water | 20 |
| Antioxidant | q.s. |
| Perfume | q.s. |

[Manufacturing method]
The oily components and the powder components in the formulation shown above were mixed, and pulverized and dispersed using a media-agitating mill. The composition thus obtained was then combined with the aqueous phase components and emulsified to obtain an emulsified liquid foundation (W/O).

As described above, a sunscreen cosmetic of the present invention is obtained by means of an incorporation of a composite powder of a micro particle zinc oxide which is coated with a silicic anhydride and whose surface is treated with a silicone, a dispersing treatment in an oil or water using a media-agitating mill or a high pressure dispersing machine and/or an incorporation of a polyoxyalkylene-modified polysiloxane. Accordingly, a sunscreen cosmetic of the present invention has an excellent ultraviolet rays protection effect as reflected by its SPF and PFA as well as the transparency and the system stability.

What is claimed is:

1. A sunscreen cosmetic comprising:
    a composite powder of a micro particle zinc oxide which is coated with a silicic anhydride and whose surface is treated with a silicone,
    wherein said composite powder is dispersed in an oil or water using a media-agitating mill or a high pressure dispersing machine.

2. A sunscreen cosmetic according to claim 1, wherein said composite powder is a composite powder obtained by coating a micro particle zinc oxide having a particle size of 0.1 μm or less with a silicic anhydride at a coating rate of 5 to 30 wt % followed by a surface treatment with 3 to 12 wt % of a silicone.

3. A sunscreen cosmetic according to claim 1, wherein said composite powder of a micro particle zinc oxide treated with a silicic anhydride and a silicone is in an amount of 3 to 30 wt %.

4. A sunscreen cosmetic according to claim 1, wherein 1 wt % or more of a powder whose surface is treated with one or more substances selected from fatty acids, fatty acid soaps and fatty acid esters is further contained.

5. A sunscreen cosmetic according to claim 1, wherein 0.1 wt % or more of one or more substances selected from fatty acids, fatty acid soaps and fatty acid esters are further added as powder dispersing agents.

6. A sunscreen cosmetic according to claim 2, wherein said composite powder of a micro particle zinc oxide treated with a silicic anhydride and a silicone is in an amount of 3 to 30 wt %.

7. A sunscreen cosmetic according to claim 2, wherein 1 wt % or more of a powder whose surface is treated with one or more substances selected from fatty acids, fatty acid soaps and fatty acid esters is further contained.

8. A sunscreen cosmetic according to claim 3, wherein 1 wt % or more of a powder whose surface is treated with one or more substances selected from fatty acids, fatty acid soaps and fatty acid esters is further contained.

9. A sunscreen cosmetic according to claim 2, wherein 0.1 wt % or more of one or more substances selected from fatty acids, fatty acid soaps and fatty acid esters are further added as powder dispersing agents.

10. A sunscreen cosmetic according to claim 3, wherein 0.1 wt % or more of one or more substances selected from fatty acids, fatty acid soaps and fatty acid esters are further added as powder dispersing agents.

11. A sunscreen cosmetic comprising:
a composite powder of a micro particle zinc oxide which is coated with a silicic anhydride and whose surface is treated with a silicone,
wherein said sunscreen cosmetic is comprised of a polyoxyalkylene-modified polysiloxane and/optionally wherein said composite powder is dispersed in an oil or water using a media-agitating mill or a high pressure dispersing machine.

12. A sunscreen cosmetic according to claim 11, wherein said-polyoxyalkylene-modified polysiloxane is one or more selected from those represented by Formula [1]:

[1]

wherein R denotes a methyl group or partly a phenyl group, R' denotes hydrogen or an alkyl group having 1 to 12 carbon atoms, p denotes an integer of 1 to 5, q denotes an integer of 2 to 3, and x, m and n denote mean numbers giving a polyoxyalkylene-modified organopolysiloxane which contains in its molecule 5 to 40 wt % of the polyoxyalkylene group and whose molecular weight is 2000 or more.

13. A sunscreen cosmetic according to claim 11, wherein said polyoxyalkylene-modified polysiloxane is in an amount of 0.5 to 7 wt %.

14. A sunscreen cosmetic according to claim 12, wherein said composite powder is a composite powder obtained by coating a micro particle zinc oxide having a particle size of 0.1 μm or less with a silicic anhydride at a coating rate of 5 to 30 wt % followed by a surface treatment with 3 to 12 wt % of a silicone.

15. A sunscreen cosmetic according to claim 12, wherein said composite powder of a micro particle zinc oxide treated with a silicic anhydride and a silicone is in an amount of 3 to 30 wt %.

16. A sunscreen cosmetic according to claim 12, wherein 1 wt % or more of a powder whose surface is treated with one or more substances selected from fatty acids, fatty acid soaps and fatty acid esters is further contained.

17. A sunscreen cosmetic according to claim 13, wherein 1 wt % or more of a powder whose surface is treated with one or more substances selected from fatty acids, fatty acid soaps and fatty acid esters is further contained.

18. A sunscreen cosmetic according to claim 12, wherein 0.1 wt % or more of one or more substances selected from fatty acids, fatty acid soaps and fatty acid esters are further added as powder dispersing agents.

19. A sunscreen cosmetic according to claim 13, wherein 0.1 wt % or more of one or more substances selected from fatty acids, fatty acid soaps and fatty acid esters are further added as powder dispersing agents.

* * * * *